US00PP37119P2

(12) United States Plant Patent
Vele

(10) Patent No.: US PP37,119 P2
(45) Date of Patent: Dec. 2, 2025

(54) ***ALSTROEMERIA* PLANT NAMED 'TURCAL211'**

(50) Latin Name: *Alstroemeria hybrida*
Varietal Denomination: TURCAL211

(71) Applicant: Ernest Turc S.A.S., Maze-Milon (FR)

(72) Inventor: Mathieu Vele, Angers (FR)

( * ) Notice: Subject to any disclaimer, the term of this patent is extended or adjusted under 35 U.S.C. 154(b) by 0 days.

(21) Appl. No.: 19/054,474

(22) Filed: Feb. 14, 2025

(51) Int. Cl.
*A01H 5/02* (2018.01)
*A01H 6/56* (2018.01)

(52) U.S. Cl.
USPC ..... Plt./309
CPC ..... *A01H 6/564* (2018.05)

(58) Field of Classification Search
USPC ..... Plt./309
CPC ..... A01H 5/02
See application file for complete search history.

*Primary Examiner* — Kent L Bell

(57) ABSTRACT

A new and distinct cultivar of *Alstroemeria* plant named 'Turcal211' is disclosed, characterized by uniquely low growing/compact plants with excellent pot and garden performance. Plants are very floriferous with a long flowering period from June to October. Flowers are bright cherry red with a yellow center with stripes. Hardiness to −12° C. has been observed. Foliage is healthy and green, also during the flowering period. The new variety is an *Alstroemeria*, typically produced as an outdoor ornamental plant.

2 Drawing Sheets

Latin name of the genus and species: *Alstroemeria hybrida.*

Variety denomination: 'TURCAL211'.

BACKGROUND OF THE INVENTION

The new cultivar is the product of a planned breeding program. The intention of the program was to create new *Alstroemeria* varieties which are compact, hardy, and free flowering. The cross pollination resulting in the new cultivar was conducted by the inventor at a nursery in Mazé-Milon, France during May of 2012 at a research nursery. The seed parent is the unpatented proprietary *Alstroemeria hybrida* referred to as '10004'. The pollen parent is the unpatented proprietary *Alstroemeria hybrida* referred to as '10003'. The new cultivar 'TURCAL211' was selected by the inventor in 2016 at the same location in Mazé-Milon, France.

The first asexual reproduction was performed by tissue culture in 2016, at the same nursery in Mazé-Milon, France. The inventor continued controlled testing and propagation, assessing stability of the unique characteristics of this variety. Multiple generations have been reproduced and have shown that the unique features of this cultivar are stable and reproduced true to type.

The inventor has filed an application with the CPVO Aug. 27, 2020, having application number 2020/1770. 'TURCAL211' was not sold until 2024 due to a lack of commercial propagative material and distribution. The first sale was directly or indirectly from the inventor. This disclosure falls within the exception allowed under 102(b)(1).

SUMMARY OF THE INVENTION

The cultivar 'TURCAL211' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Turcal211'. These characteristics in combination distinguish 'TURCAL211' as a new and distinct *Alstroemeria* cultivar:

1. Dwarf/compact plant that stays very low.
2. Excellent pot and garden performance.
3. Long flowering period from June to October.
4. Sturdy growth without floppy stems.
5. Very floriferous producing a bright cherry red flower with a yellow center with stripes.
6. Hardy to −12° C.

PARENT COMPARISON

Plants of the new cultivar 'TURCAL211' are similar to the seed parent in most horticultural characteristics. 'TURCAL211', however, differs in the following:

1. Flowers of the new variety are larger than flowers of the seed parent.
2. Flower color of the new variety is bright cherry red with a yellow center with stripes; flower color of the seed parent is pink and white with a yellow center.
3. Plants of the seed parent are about ⅓ taller than plants of the new cultivar.

Plants of the new cultivar 'TURCAL211' are similar to the pollen parent in most horticultural characteristics. 'TURCAL211', however, differs in the following:

1. Flower color of the new variety is bright cherry red with a yellow center with stripes; flower color of the pollen parent is violet with no yellow throat.
2. Plants of the pollen parent are about ⅓ taller than plants of the new cultivar.

COMMERCIAL COMPARISONS

Plants of the new cultivar 'TURCAL211' can be compared to the commercial variety *Alstroemeria* 'Compact Machu', unpatented. Plants of these cultivars are similar in most horticultural characteristics, however, 'TURCAL211' differs in the following:

1. Plants of the new cultivar are not prone to yellow foliage after the flowers open, as seen in this comparator.
2. The new variety is more cold hardy than this comparator.
3. Flowers of the new cultivar are darker cherry red than flowers of this comparator.
4. Flowers of the new cultivar have a yellow center with stripes; flowers of this comparator have white streaks in the center.

Plants of the new cultivar 'TURCAL211' can be compared to the commercial variety *Alstroemeria* 'Turcal139', U.S. Plant Pat. No. 36,828. Plants of these cultivars are similar in most horticultural characteristics, however, 'TURCAL211' differs in the following:

1. The main flower color of 'TURCAL211' is bright cherry red (Red 53C mixed with 44C); the main flower color 'Turcal139' is pink/salmon (Red 41C).

BRIEF DESCRIPTION OF THE PHOTOGRAPHS

This new *Alstroemeria* is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Alstroemeria*.

DETAILED BOTANICAL DESCRIPTION

Figure 1:
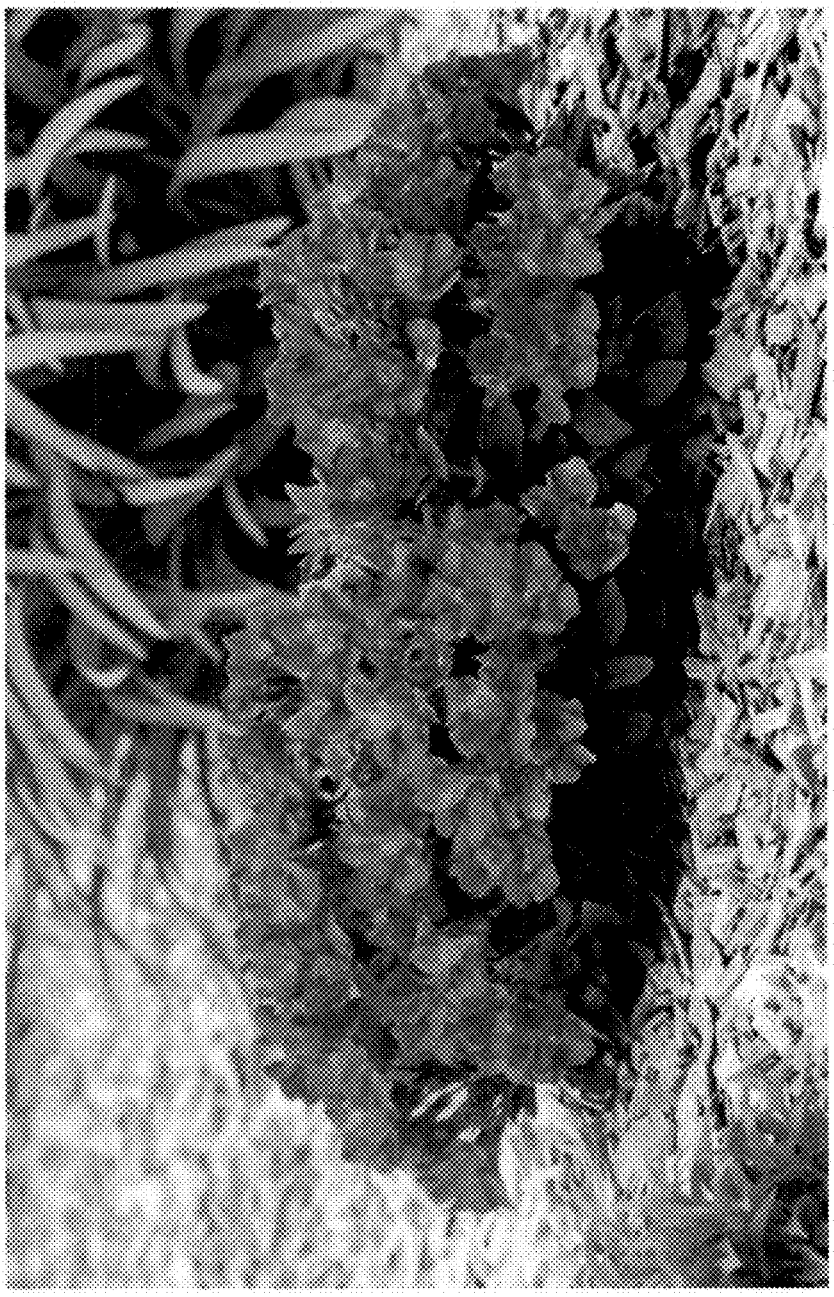
FIG. 1 is a color photograph of a flowering plant of 'TURCAL211' in in the ground during Summer in Gien, France. The plant is approximately 2 years old.
Figure 2:
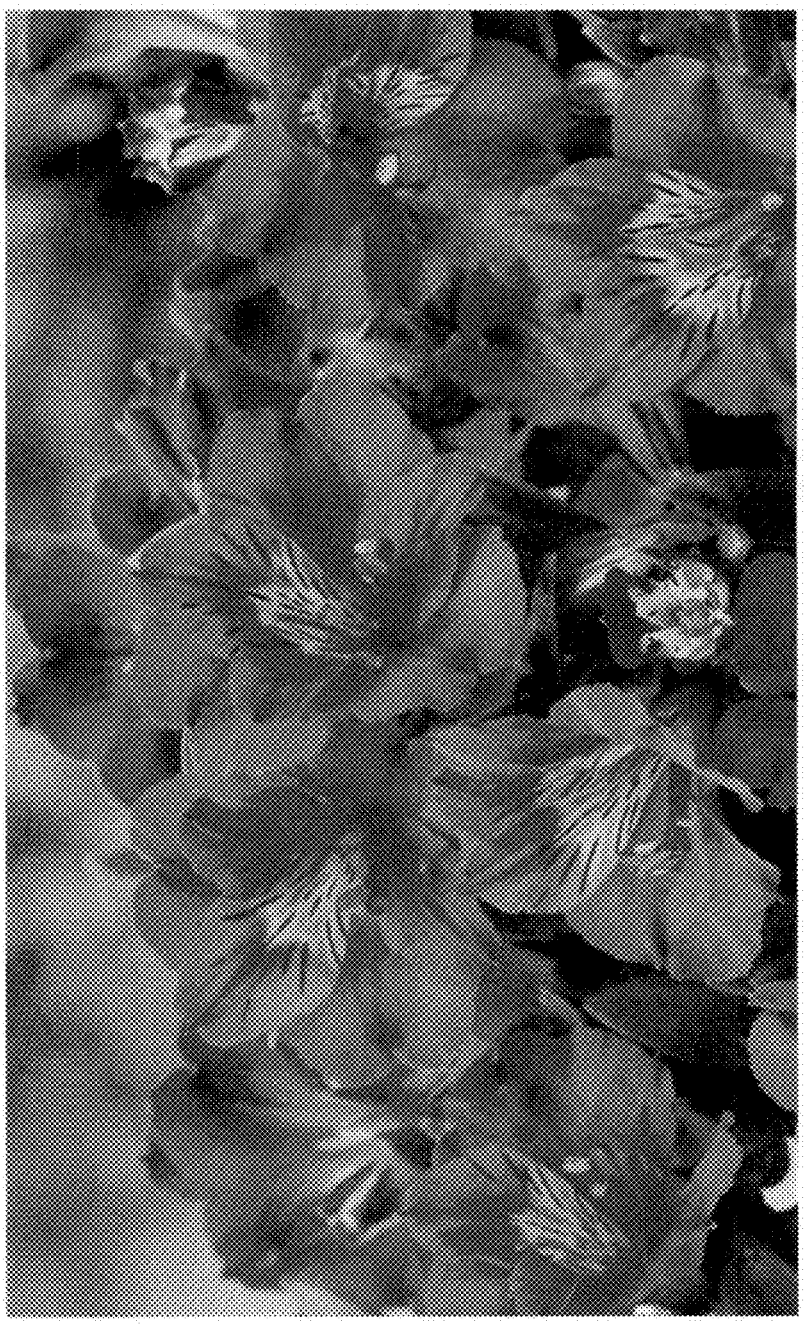
FIG. 2 is a color photograph showing a close-up view of a multiple flowers of 'TURCAL&b 211'.

In the following description, color references are made to The Royal Horticultural Society Colour Chart 2015, except where general terms of ordinary dictionary significance are used. The following observations and measurements describe 'TURCAL211' plants grown in 13 cm pots in Gien, France. Plants were approximately 4 to 5 months old. Temperatures ranged from approximately 3° C. to 22° C. at night and 10° C. to 32° C. during the day. No artificial light, photoperiodic treatments were given to the plants. No chemical treatments were given to plants. Measurements and numerical values represent averages of typical plant types.

Botanical classification: *Alstroemeria hybrida* 'TURCAL211'.

PROPAGATION

Method: Tissue culture.

Time to rooted plug: About 12 weeks to produce a 3 cm plug.

Root description: Fleshy and fibrous roots present. Cream colored.

PLANT

Growth habit: Compact, dwarf flowering perennial.

Height: 22 cm. At full mature height 25 to 28 cm.

Plant spread: 20 cm. At full mature width about 40 cm.

Stem characteristics: 9 primary basally emerging stems

Length of stems: Approximately 11 cm.

Diameter of stems: Approximately 4 mm.

Texture of stems: Glabrous.

Color of stems: Near Green 137B streaked Yellow-Green 145B and 145C. Base strongly flushed 183A.

FOLIAGE

Leaf:

*Arrangement.*—Alternate.

*Average length.*—Approximately 6 cm.

*Average width.*—Approximately 1.6 cm.

*Shape of blade.*—Obovate.

*Apex.*—Acute

*Base.*—Truncate.

*Margin.*—Entire.

*Texture of top surface.*—Glabrous.

*Texture of bottom surface.*—Glabrous.

*Leaf internode length.*—1 cm.

*Attachment.*—Sessile.

*Color.*—Young foliage upper side: Near RHS Green 137A, 137C towards the base. Young foliage under side: Near RHS Green 137A, 137C towards the base. Mature foliage upper side: Near RHS Green 137A, 137C towards the base. Mature foliage under side: Near RHS Green 137A, 137C towards the base.

*Venation.*—Type: Parallel. Venation color upper side: Yellow-Green 145A. Venation color under side: Yellow-Green 145A.

FLOWER

Natural flowering season: June to October.

Inflorescence type and habit: Single cup-shaped flowers arranged in umbels. Flowers outwardly facing.

Inflorescence size:

*Diameter.*—Approximately 10.5 cm.

*Height.*—Approximately 7 cm.

Inflorescences per plant: 5 to 6 on a plant of this age.

Flowers per inflorescence: 4 to 5 on a plant of this age.

Flower longevity on plant: About 7 days, after fully opened.

Flower size:

*Diameter.*—Approximately 5.5 cm.

*Length.*—Approximately 4.8 cm.

Perianth/petals:

*Arrangement.*—Six arranged in two whorls, each whorl with two lateral and one median segment.

*Inner lateral segment size.*—4.8 cm long and 2 cm wide. Shape: Obovate. Margin: Finely dentate. Very slightly undulating. Apex: Mucronate. Base: Attenuate. Texture: Glabrous all surfaces. Color: When opening, upper side: Red-Purple 60A and 60B (mixed together). Towards the bottom Yellow 4C. Stripes Greyed-Purple 183A. When opening, under side: Red-Purple 60B. Towards the bottom Yellow 4C. Fully opened, upper side: Red 53C, center Red 44C. Base Yellow 4A blotched Red 44C. Stripes Greyed-Purple 183A. Fully opened under side: Red 53C, center Red 44C. Base Yellow 4A blotched Red 44C with a very small blotch of Yellow 4A.

*Outer lateral segment size.*—4.6 cm long and 3 cm wide. Shape: Wishbone-shaped. Margin: Entire, very slightly undulate. Apex: Mucronate. Base: Attenuate. Texture: Glabrous. Color: When opening, upper side:

Red-Purple 60A and 60B (mixed together). Towards the bottom Yellow 4C. When opening, under side: Red-Purple 60B. Towards the bottom Yellow 4C. Fully opened, upper side: Red-Purple 60B and 61B (mixed together). Base fades 61C and 61D. Fully opened under side: Red-Purple 60D. Tips and veins Green 137C.

*Outer median segment size.*—4.6 cm long and 3 cm wide. Shape: Spatulate. Margin: Lower half entire, upper half finely dentate. Undulate. Apex: Mucronate. Base: Attenuate. Texture: Glabrous. Color: When opening, upper side: Red-Purple 60A and 60B (mixed together). Towards the bottom Yellow 4C. When opening, under side: Red-Purple 60B. Towards the bottom Yellow 4C. Fully opened, upper side: Red-Purple 60B and 61B (mixed together). Base fades 61C and 61D. Fully opened under side: Red-Purple 60D. Tips and veins Green 137C.

*Inner median segment.*—Size: 4 cm long and 2 cm wide. Shape: Spatulate. Margin: Lower half entire, upper half finely dentate. Undulate. Apex: Rounded. Base: Attenuate. Texture: Glabrous. Color: When opening, upper side: Red-Purple 60A. Center streaked 59A. Base Yellow 4C. When opening, under side: Red-Purple 60B. Base Yellow 4C. Fully opened, upper side: Red-Purple 60A. Center streaked 59B. Fully opened under side: Red-Purple 60B.

Bud:

*Shape.*—Ovoid.
*Length.*—Approximately 1.5 cm.
*Diameter.*—Approximately 8 mm.
*Texture.*—Smooth, glabrous.
*Color.*—Near RHS Yellow-Green 145C flushed 145B and 145A. Hints of Green 137C and Red-Purple 71A towards the top.

Fragrance: None.

Peduncle:

*Length.*—4 cm.
*Diameter.*—3 mm.
*Color.*—Green 137C with occasional hint of 71A.
*Texture.*—Glabrous.

Pedicel:

*Length.*—1 to 1.5 cm.
*Diameter.*—2 to 3 mm.
*Color.*—Green 137C with occasional hint of 71A.
*Texture.*—Glabrous.

REPRODUCTIVE ORGANS

Stamens:

*Number.*—6.
*Filament length.*—Approximately 3.1 cm.
*Filament color.*—Near RHS Purple 71A and 71B.

Anthers:

*Length.*—4 mm.
*Color.*—Near RHS Greyed-Orange 163B.
*Pollen.*—Color: Near Greyed-Orange 163B. Quantity: Scant.

Pistil:

*Number.*—1.
*Length.*—Approximately 3.5 cm.
*Style.*—Length: Approximately 3.2 cm. Color: Near RHS Purple 71B, 71A at top.
*Stigma.*—Shape: 3-parted. Diameter: 7 mm. Color: Near RHS Red-Purple 71B. Ovary Color: Near RHS Green 137C.

OTHER CHARACTERISTICS

Fruit: Not observed

Seed: Not observed.

Disease/pest resistance: Neither resistance nor susceptibility to normal diseases and pests of *Alstroemeria* has been observed.

Temperature tolerance: Cold hardy to −12° C.

Drought tolerance: Tolerance for drought not tested.

What is claimed is:

1. A new and distinct cultivar of *Alstroemeria* plant named 'Turcal211' as herein illustrated and described.

* * * * *